US00PP16160P3

(12) United States Plant Patent
Roberts

(10) Patent No.: US PP16,160 P3
(45) Date of Patent: Dec. 13, 2005

(54) APRICOT TREE 'H 1995 CV'

(50) Latin Name: *Prunus armenica*
Varietal Denomination: H 1995 cv

(75) Inventor: Harry Roberts, Alexandra (NZ)

(73) Assignee: Nevis Fruit Company USA LLC, Boulder, CO (US)

( * ) Notice: Subject to any disclaimer, the term of this patent is extended or adjusted under 35 U.S.C. 154(b) by 78 days.

(21) Appl. No.: 10/846,087

(22) Filed: May 14, 2004

(65) Prior Publication Data

US 2005/0257300 P1 Nov. 17, 2005

(51) Int. Cl.[7] ..... A01H 5/00

(52) U.S. Cl. ..... Plt./186

(58) Field of Search ..... Plt./186

*Primary Examiner*—Anne Marie Grunberg
(74) *Attorney, Agent, or Firm*—Wells St. John P.S.

(57) ABSTRACT

A new and distinct of apricot tree is disclosed and which is mature for harvesting and shipment under the ecological conditions prevailing in Eastern Washington, about July 18$^{th}$.

4 Drawing Sheets

BACKGROUND OF THE NEW VARIETY

The present invention relates to a new and distinct variety of apricot tree, *'Prunus armenica'* and which has been denominated varietally as 'H 1995 cv' hereinafter, and more specifically to a new apricot tree which is characterized as to novelty by bearing large red-blushed apricots having good shelf life, and which are ripe for harvesting and shipment under the ecological conditions prevailing in Eastern Washington on or about July 18$^{th}$.

ORIGIN AND ASEXUAL REPRODUCTION

The present variety of apricot tree was discovered by me as a chance seedling growing in a cultivated area of my property which is located in Earnscleough, Alexandra, Central Otago, New Zealand in 1988. The chance seedling was an open pollinated seedling of unknown parentage and which was found growing in an orchard of "Sundrop" apricot trees (not patented). This chance seedling was subsequently transplanted to a trial row on the same property where it first produced fruit which could be observed during January of 1994. During the 1995 growing season, continued evaluations of the chance seedling confirmed that the chance seedling produced noteworthy fruit having a larger size, and a more attractive skin color, and which further had good storage qualities. After the 1995 growing season, budwood from the original tree was submitted to the quarantine facility, IR-2, at Prosser, Wash. for further testing to determine the presence of any viruses. Virus certified-free material was released in 1997, and test trees were budded into a test plot which is currently located near Ephrata, Wash. in 1999. Second generation trees have been grafted onto "Manchurian" rootstock (not patented). These subsequent progeny have proven to be true to the original chance seedling in all respects.

SUMMARY OF THE VARIETY

The new variety of apricot tree is characterized as to novelty, and is otherwise deemed noteworthy by producing large, attractively colored fruit, which are ripe for harvesting and shipment under ecological conditions prevailing in Ephrata, Wash. on July 18$^{th}$. This date of maturity is similar to that of the "Goldrich" apricot tree (not patented) and about two weeks after the "Perfection" apricot tree (not patented), at the same geographical location. The present variety of apricot tree is most closely similar to the "Perfection" apricot tree, but which is distinguishable from the apricot variety "Perfection" by producing fruit which are ripe for harvesting and shipment about 14 days after the harvesting of the variety "Perfection" under the ecological conditions prevailing at my orchard in New Zealand. Further, the present variety is distinguished from the variety "Sundrop" by being ripe for harvesting and shipment about 30 days later after the "Sundrop" variety under the same ecological conditions.

BRIEF DESCRIPTION OF THE DRAWINGS

The accompanying drawings are color photographs of various aspects of the present plant. The colors are as nearly true as is reasonably possible in color representations of this type. Due to chemical development, processing and printing, the leaves and fruit of the present tree may, or may not be, accurate when compared to the actual specimen. For this reason, future color references should be made to the color plates as provided by the Munsell Book of Color, and the other general color descriptions as provided for hereinafter.

DETAILED DESCRIPTION

Referring more specifically to the pomological details of this new and distinct variety of apricot tree, the following has been observed during the 2003 growing season under the ecological conditions prevailing in a test orchard which is located near Ephrata, Wash. All major color code designations are by reference to the Munsell Book of Color. Common color names are also used occasionally.

TREE

Tree size: Considered typical for the variety. Second generation trees in their fifth leaf (5 years in the field) have a height of about 3 to about 4 meters; and a width of about 2 to about 3.5 meters.

Productivity: Considered average. About 3 to about 4 kilograms per tree were harvested in the fourth leaf.

Vigor: Considered vigorous. The present variety shows about 1 to about 1.5 meters of annual growth of fifth leaf trees which have been grafted onto "Manchurian" (unpatented) rootstock.

Growing habit: Considered spreading.

Chilling requirement: Average for the variety. This is based upon observations of the growth of the new variety as seen in New Zealand; and in the state of Washington. Actual chilling requirements have not been determined. The chilling requirement does not appear to be distinctive of the present variety.

Regularity of bearing: Considered regular and uniform.

TRUNK

Size: Considered average for this variety. The present tree was about 5 cm. in diameter when measured at a distance of about 0.3 meters from the surface of the ground.

Bark color: Brown (5 YR 5/4).

Lenticels:

*Color.*—Light tan (7.5 YR 8/2).

*Density.*—About 3 lenticels per square cm may be found.

*Size.*—Elongated and having a length dimension of about 3 mm. and a width dimension of about 1 mm.

BRANCHES

Growth habit: Vigorous, and spreading, which is typical for most apricot trees.

Bark color: Immature Branches— Green (2.5 GY 4/6), and occasionally purple (7.5 R 3/6) with increasing senescence. As immature wood becomes more mature, the bark color turns to brown (7.5 YR 4/4).

Pubescence: Not observed.

Figure 6:
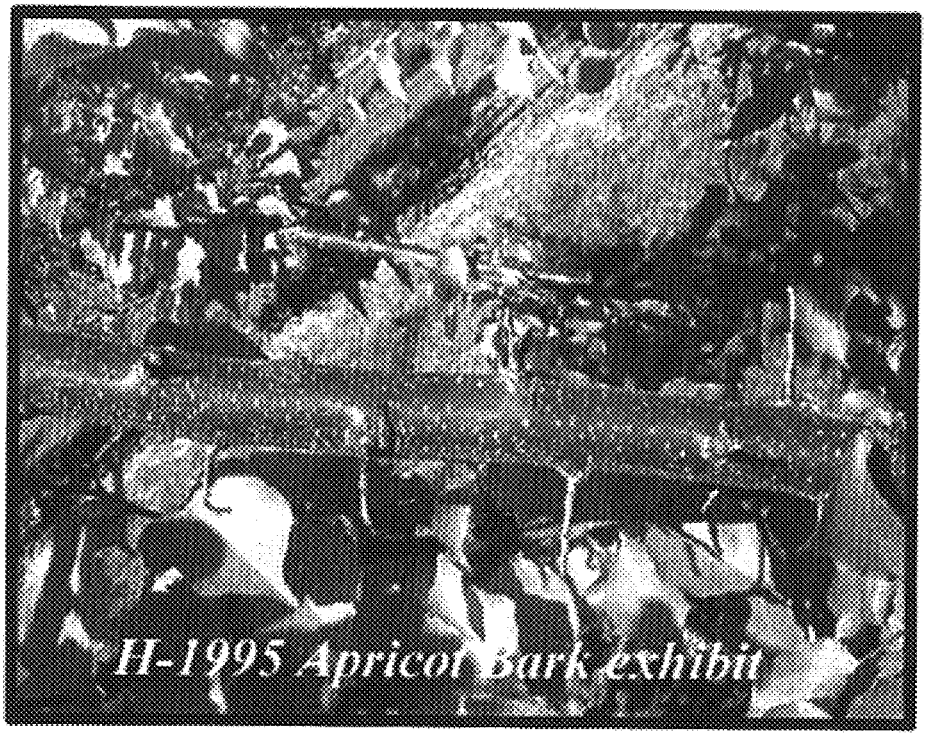
FIG. 6 shows the bark characteristics of two year old wood.

Bark lenticels:

*Numbers.*—Average, on one year or older wood, approximately 8 lenticels may be found per square cm. (FIG. 6).

*Size.*—Small, and round and having a diameter of less than about 0.5 mm.

Lenticels:

*Color.*—Tan (10 YR 7/4).

Internodes:

*Length.*—About 1.5 to about 2 cm. when measured on vigorous current season shoots.

LEAVES

Leaf size:

*Generally.*—Considered medium to large for the species. Mature leaves have length dimension of about 4.5 to about 7.4 cm.; and a width of about 5.0 to about 8.0 cm.

Leaf form: Considered to be a typical apricot leaf shape, and having an acuminate tip, and a straight base, which may on occasion also appear slightly indented. The leaf blade is normally bent.

Mature leaf color:

*Dorsal surface.*—Light green (5 GY 7/6).

*Ventral surface.*—A grey-green (5 GY 7/4).

*Mid vein.*—Typically considered reddish purple (5 GY 8/4), and occasionally tinged with purple coloration (2.5 R 3/10).

Immature leaf color: These leaves typically have a pinkish purple color which fades to green with increasing senescence. This color is not distinctive of the variety, however.

Marginal form: Considered finely crenate. Approximately 8 serrations may be found per cm. The leaf margin is often wavy in appearance.

Mid-vein thickness: About 1 mm. when measured at the base. The mid-vein tapers as it proceeds toward the tip of the leaf.

Leaf glandular characteristics: Approximately 2 to about 5 round glands are found per petiole. These glands are typically located singly or occasionally in pairs along the dorsal surface of the petiole.

Leaf glands:

*Color.*—Typically purple (5 R 3/6).

Stipules: Not present.

Leaf petiole:

*Size.*—Considered average for the variety, approximately 1 to about 2 mm. in diameter; and further having a length dimension of about 3 to about 4 cm.

*Color.*—Considered reddish purple (2.5 R 3/10).

FLOWER

Time of bloom: Date of full bloom was observed on Mar. 22, 2003 under the prevailing ecological conditions existing near Ephrata, Wash. First Bloom was observed on Mar. 17, 2003. Petal fall was observed on Mar. 28, 2003. The flowers have no apparent fragrance.

Dormant flower buds:

*Size.*—In the dormant state, the flower buds are about 1.5 mm in width, and about 3.5 mm. in length.

*Surface texture.*—Considered globose.

*Color.*—In the dormant condition the flower buds have brown color (2.5 YR 2/4). In the popcorn stage, the flower buds have a light pink color (2.5 R 9/2).

Size of flower: In a fully opened state the flower is about 20 to 30 mm. in diameter at full bloom. This is best seen by reference to FIG. 7.

Flower petals:

*Length.*—About 15 mm.

*Width.*—About 20 mm.

Figure 7:
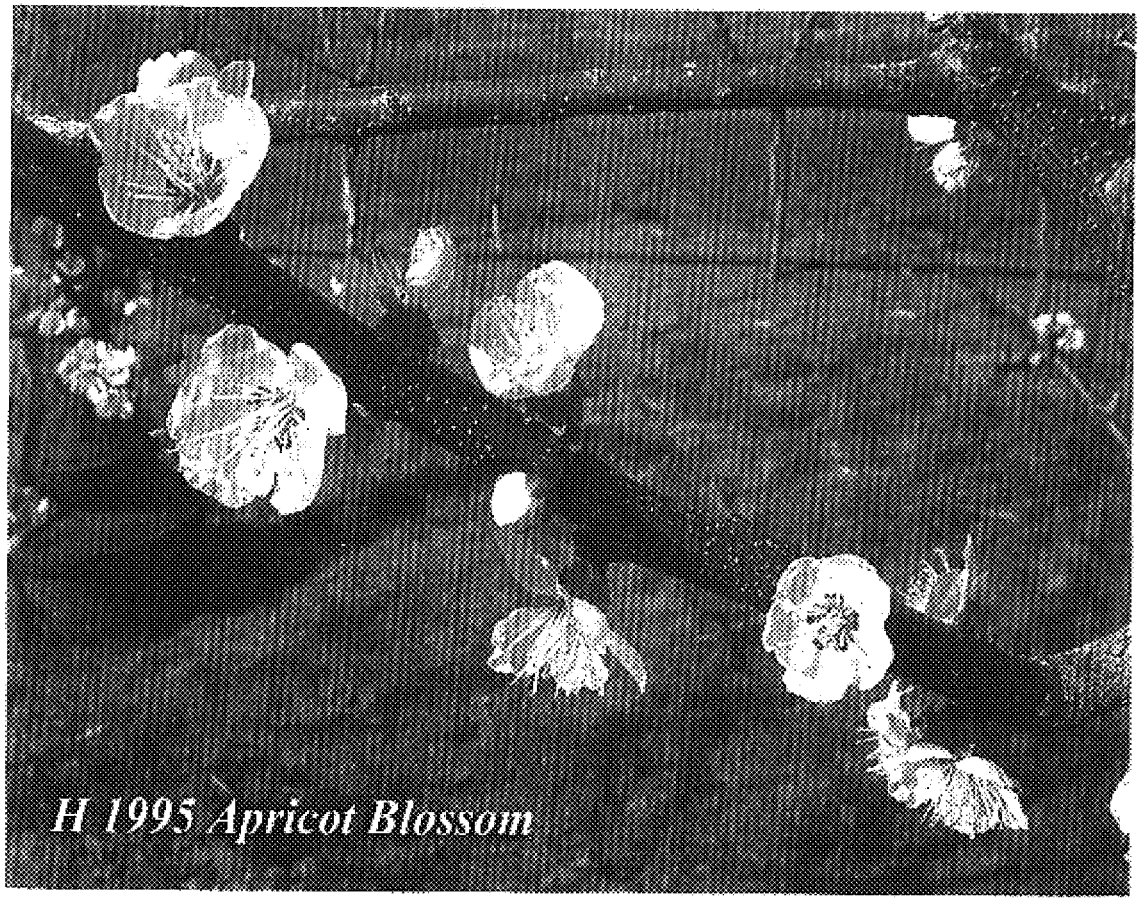
FIG. 7 shows the blossom characteristics of the present variety of apricot tree in full bloom and as seen on Apr. 3, 2003 at the test orchard which is located near Epharata, Wash.

*Color.*—Light pink at the popcorn stage (2.5 R 9/2), and white when fully opened, this is seen in FIG. 7.

Sepals:
*Color.*—Bright red (5 R 4/14).
Stamens:
*Numbers.*—About 14 to about 20 stamens will be found per flower.
Filaments:
*Numbers.*—Approximately 25 are found per flower.
*Length.*—About 10 mm.
Anthers:
*Color.*—Yellow (5 Y 5/12).
Pistil:
*Length.*—About 15 mm.
Stigma:
*Length.*—About 1.7 mm.

FRUIT

Figure 1:
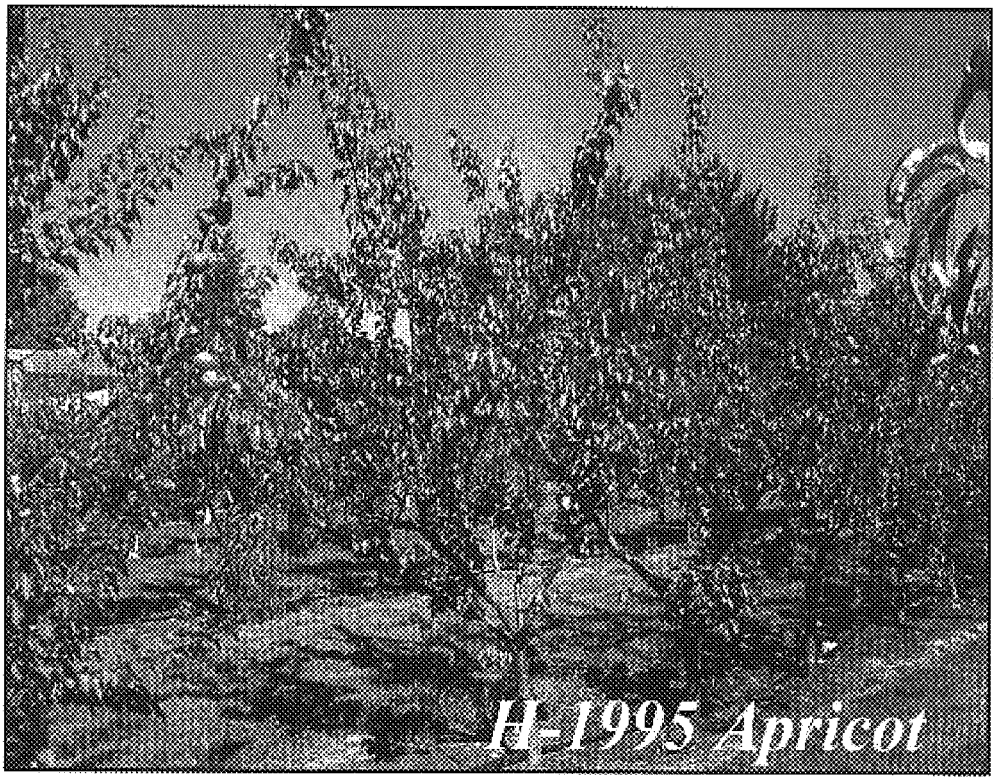
FIG. 1 shows the growing habit of three year old, second generation trees growing at a test orchard near Ephrata, Wash. on Jul. 18, 2003.
Figure 2:
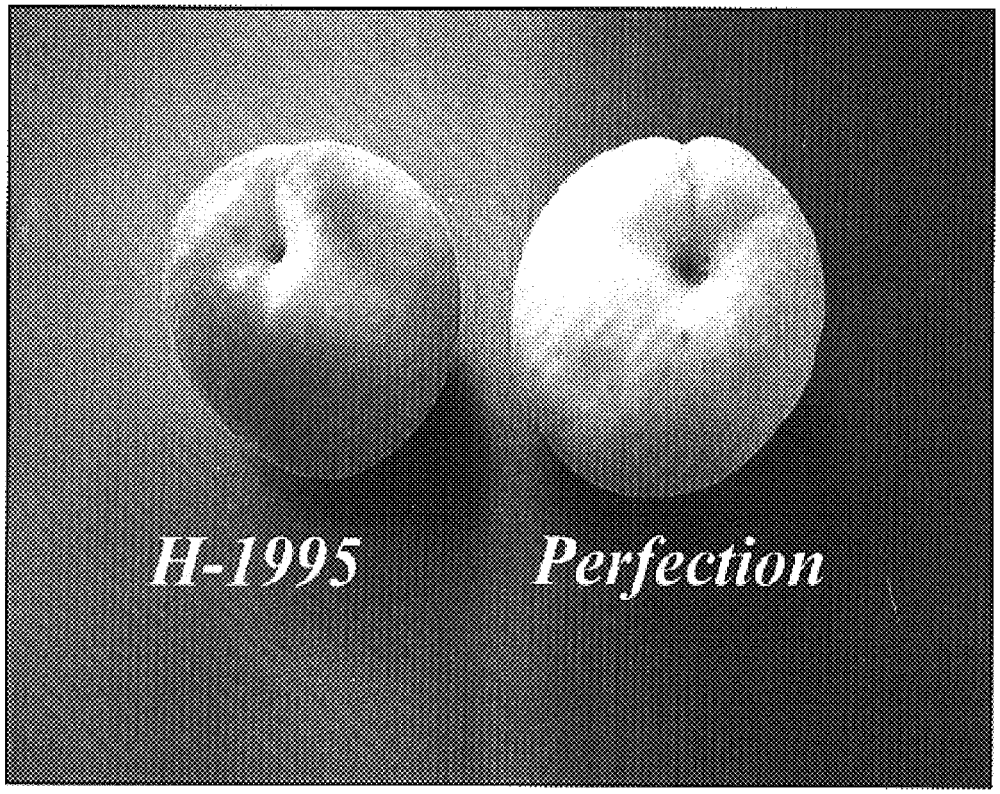
FIG. 2 is a photograph which shows one of the fruit produced by the present variety of apricot tree next to that produced by the "Perfection" apricot tree.
Figure 3:
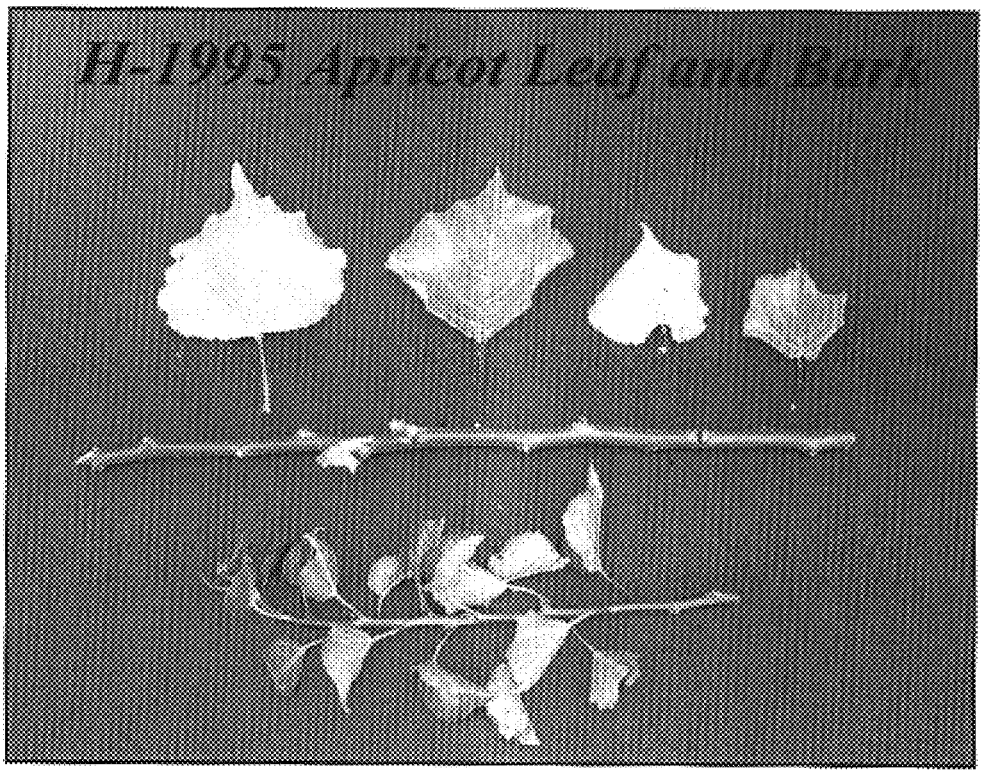
FIG. 3 shows the dorsal and ventral surfaces of both mature (top) and immature leaves, (bottom) of the new variety of apricot tree.
Figure 4:
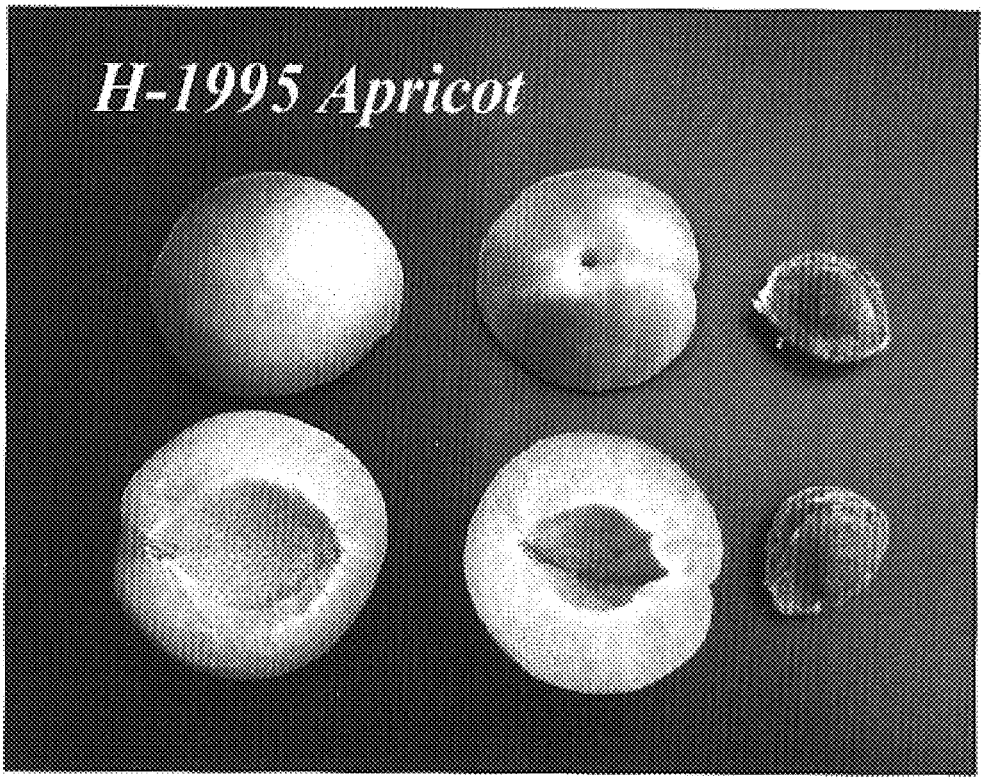
FIG. 4 shows several fruit of the present variety and which are individually divided in the transverse and longitudinal planes and further showing the stone thereof.
Figure 5:
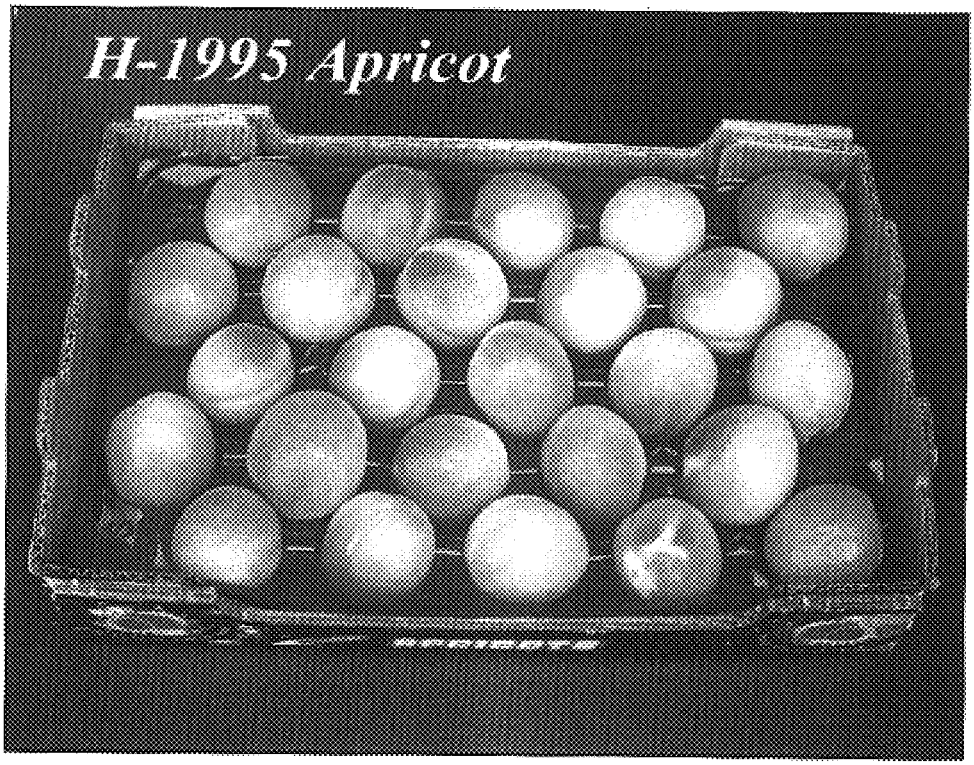
FIG. 5 depicts the fruit of the present variety of apricot tree as would be seen in a mature shipping ripe condition.

Maturity when described: Generally, the fruit produced by the present variety of apricot tree is described as it will be found at full commercial maturity. In this regard, the fruit of the present variety was ripe for harvesting and shipment under the ecological conditions prevailing near Ephrata, Wash. on Jul. 18, 2003. The harvesting date is considered to be similar to that of the "Goldrich" apricot variety (unpatented); and about 2 weeks after the "Perfection" apricot variety (unpatented) growing at the same geographical location.
Fruit size: Considered large for the species. The average weight of the fruit which was harvested in the 2003 was about 88 grams.
Fruit dimensions: Length about 60 mm.; width about 55 mm.; and thickness of about 47 mm.
Fruit form: Round, and considered oblong. The fruit form is similar to that produced by the "Perfection" apricot tree. The fruit is otherwise considered to be symmetrical.
Suture:
*Generally.*—Considered shallow and about 1 to 2 mm. deep.
Stem cavity:
*Depth.*—About 6 mm.
*Width.*—About 16 mm.
Skin:
*Thickness.*—Considered thin and tender.
*Texture.*—Smooth and occasionally slightly bumpy.
Skin blush color: The present variety has a distinctive pinkish blush (5 R 5/13). This blush may be found on a majority of the fruit, and covers approximately 20 to about 50% of the fruit surface. This is in contrast to the fruit produced by the "Perfection" apricot tree as seen in FIG. 2. This blush is further seen in FIGS. 4 and 5, respectively.
Ground color: Yellow-orange (2.5 Y 8.5/12).
Tendency to crack: Not observed.
Flesh color: Orange (7.5 YR 7/12).
Juice production: Considered moderately juicy. Sugar levels are measured at about 13 to about 15 degrees brix. This characteristic appears to be superior to the fruit produced by the "Perfection" apricot tree growing at the same geographical location.
Aroma: Variable, none to mild.
Flesh texture: Melting, and although occasionally, it may appear slightly crunchy, depending upon the degree of ripeness.
Fibers:
*Generally.*—None noted.
Ripening characteristics: Considered uniform.
Eating quality: Considered very good and superior to the fruit produced by the "Perfection" apricot tree.

STONE

Attachment: Considered freestone. The stone may appear attached slightly at the base and slightly along the ridges thereof.
Stone size: Considered medium, and similar to the stone as found in the fruit produced by the "Perfection" apricot tree.
Stone length: About 30 mm.
Stone width: About 25 mm.
Stone thickness: About 15 mm.
Stone form: Ovoid.
Base shape: Acute.
Apex shape: Blunt, and occasionally rounded.
Stone side-shape: Considered equal.
Stone surface texture: Medium to smooth.
Surface color: Brown (7.5 YK 5/8).
Pit color: Light tan (7.5 YR 7/6).
Pit-form: Plump, and having a bitter, almond flavor, and hard shell.
Intended use: The present variety produces fruit which appears to be useful for the commercial market.
Disease and insect resistance: No susceptibilities were noted.
Keeping quality: Considered good, the present variety has been kept in cold storage for as long as 2 weeks.

Although the new variety of apricot tree possesses the described characteristics noted above when grown in Ephrata, Wash., it is to be understood that variations in the usual magnitude and characteristics incident to growing conditions, fertilization, pruning and pest control are to be expected.

Having thus described and illustrated my new variety of apricot tree, what I claim is new and desire to secure by Plant Letters Patent is:

1. A new and distinct variety of apricot tree substantially as illustrated and described and which matures for harvesting and shipment about July $18^{th}$ under the ecological conditions prevailing in Eastern Washington, and which further has an attractive orange skin color, with a distinctive blush.

* * * * *